US010967168B2

(12) United States Patent
Kunschak

(10) Patent No.: US 10,967,168 B2
(45) Date of Patent: Apr. 6, 2021

(54) MEDICAL FLUID CONTROL DEVICE AND A PARTICULATE FILTER FOR SAME

(71) Applicant: B. Braun Melsungen AG, Melsungen (DE)

(72) Inventor: Ralf Kunschak, Willisau (CH)

(73) Assignee: B. BRAUN MELSUNGEN AG, Melsungen (DE)

(*) Notice: Subject to any disclaimer, the term of this patent is extended or adjusted under 35 U.S.C. 154(b) by 0 days.

(21) Appl. No.: 15/554,648

(22) PCT Filed: Feb. 17, 2016

(86) PCT No.: PCT/EP2016/053387
§ 371 (c)(1),
(2) Date: Aug. 30, 2017

(87) PCT Pub. No.: WO2016/139064
PCT Pub. Date: Sep. 9, 2016

(65) Prior Publication Data
US 2018/0071510 A1    Mar. 15, 2018

(30) Foreign Application Priority Data
Mar. 4, 2015  (DE) .................... 10 2015 203 863.7

(51) Int. Cl.
*A61M 39/22*   (2006.01)
*F16K 11/085*  (2006.01)
(Continued)

(52) U.S. Cl.
CPC ........ *A61M 39/223* (2013.01); *A61M 5/1409* (2013.01); *F16K 11/0853* (2013.01);
(Continued)

(58) Field of Classification Search
CPC .. A61M 39/223; A61M 5/1409; A61M 5/162; A61M 2039/229; A61M 2205/75; F16K 11/0853
See application file for complete search history.

(56) References Cited

U.S. PATENT DOCUMENTS 2,704,544 A * 3/1955 Ryan ..................... A61M 5/162
                                                      210/94
4,395,260 A * 7/1983 Todd ..................... A61M 5/162
                                                      210/188
(Continued)

FOREIGN PATENT DOCUMENTS

CN    2276571 Y1    3/1998
CN    1953778 A     4/2007
(Continued)

OTHER PUBLICATIONS

German Examination Report for German Application No. 10 2015 203 863.7, dated Sep. 11, 2017, including English translation, 10 pages.
(Continued)

*Primary Examiner* — Lauren P Farrar

(57) ABSTRACT

A medical fluid control device with a fluid flow housing has at least one attachment port for attaching and removing an external medical fluid-guiding component and at least one connection port for connecting to a further functional component of the medical fluid conduction system, and with an adjustment member for controlling a flow of fluid relative to the at least one attachment port and/or the at least one connection port. A particulate filter with a pore width of between 2 μm and 15 μm is integrated in the attachment port.

17 Claims, 4 Drawing Sheets

Figure 14:
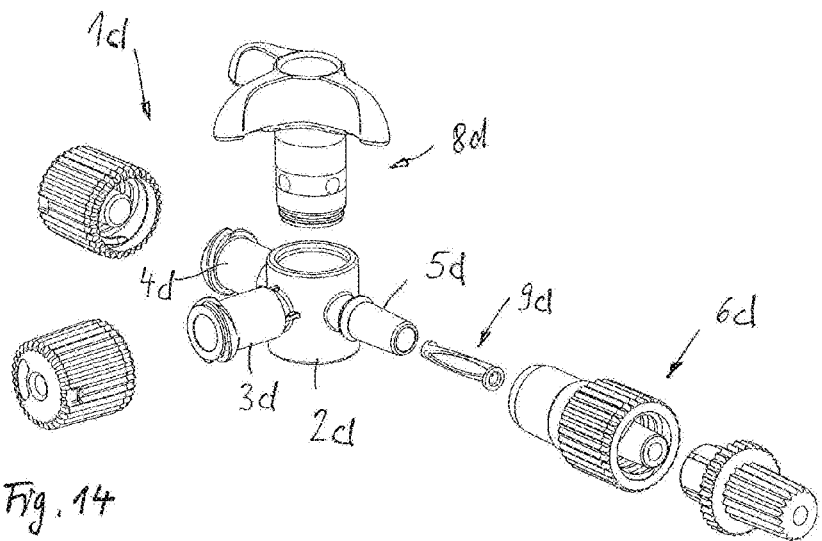

(51) Int. Cl.
    *A61M 5/14*       (2006.01)
    *A61M 5/162*      (2006.01)
(52) U.S. Cl.
    CPC ....... *A61M 5/162* (2013.01); *A61M 2039/229* (2013.01); *A61M 2205/75* (2013.01)

(56) References Cited

U.S. PATENT DOCUMENTS

| | | | |
|---|---|---|---|
| 4,581,014 | A | 4/1986 | Millerd et al. |
| 4,581,814 | A | 4/1986 | Celler et al. |
| 6,908,449 | B2 | 6/2005 | Willis et al. |
| 7,156,098 | B2 | 1/2007 | Dolezal et al. |
| 7,753,892 | B2 | 7/2010 | Newton et al. |
| 9,486,569 | B2 | 11/2016 | Eikelmann et al. |
| 2005/0205095 | A1 | 9/2005 | Dolezal et al. |
| 2005/0211250 | A1 | 9/2005 | Dolezal et al. |
| 2010/0022968 | A1 | 1/2010 | Kitani |
| 2011/0132482 | A1* | 6/2011 | Honma ................ A61M 5/385 137/605 |
| 2012/0067429 | A1 | 3/2012 | Mosler et al. |
| 2014/0360944 | A1* | 12/2014 | Esteron ................ A61K 35/14 210/698 |
| 2016/0256635 | A1* | 9/2016 | Kim .................... A61M 5/3145 |

FOREIGN PATENT DOCUMENTS

| | | | |
|---|---|---|---|
| CN | 201198942 | Y1 | 2/2009 |
| CN | 101391118 | A | 3/2009 |
| CN | 101566173 | A | 10/2009 |
| CN | 202289023 | U | 7/2012 |
| CN | 202851911 | U | 4/2013 |
| CN | 203822488 | U | 9/2014 |
| JP | 523154 | U | 1/1977 |
| JP | S5398792 | U | 8/1978 |
| JP | 60148561 | A | 8/1985 |
| KR | 20030080213 | A | 10/2003 |
| KR | 20070099652 | A | 10/2007 |
| KR | 20130002001 | U | 3/2013 |
| KR | 20130136704 | A | 12/2013 |
| KR | 200475695 | Y1 | 12/2014 |
| RU | 2113236 | C1 | 6/1998 |
| WO | 2006025054 | A2 | 3/2006 |
| WO | 2011024725 | A1 | 3/2011 |
| WO | 2014170379 | A1 | 10/2014 |

OTHER PUBLICATIONS

International Search Report and Written Opinion for International Application No. PCT/EP2016/053387, dated Apr. 25, 2016—7 Pages.
German Search Report for German Application No. 10 2015 203 863.7, dated Oct. 12, 2015 with partial translation, 9 pages.
European Examination Report for European Application No. 16706564.8, dated May 16, 2019, 6 pages.
Russian Office Action for Russian Application No. 2017131346/14(05483), dated Jul. 4, 2019 with translation, 19 pages.
Chinese Office Action for Chinese Application No. 201680026091.3, dated Nov. 29, 2019 with translation, 16 pages.
Japanese Notice of Reasons for Rejection for Japanese Application No. 2017-546174, dated Nov. 26, 2019, with translation, 13 pages.
Second Chinese Office Action received in Application No. 201680026091.3, dated Jun. 9, 2020, 19 pages. (with translation).
Korean Notice of Allowance received in Publication No. 2017-546174, dated Jun. 2, 2020, 3 pages.(with translation).

* cited by examiner

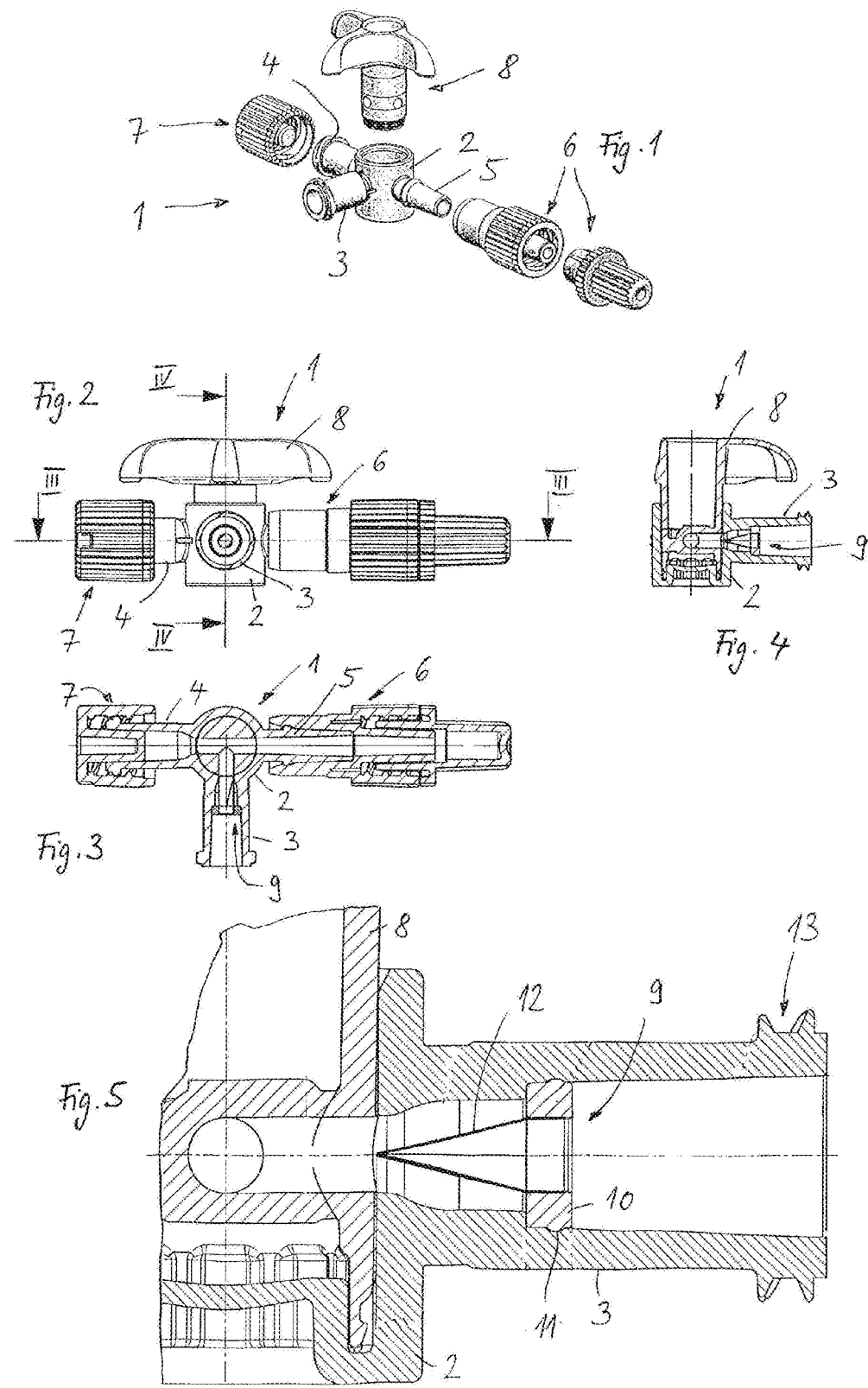

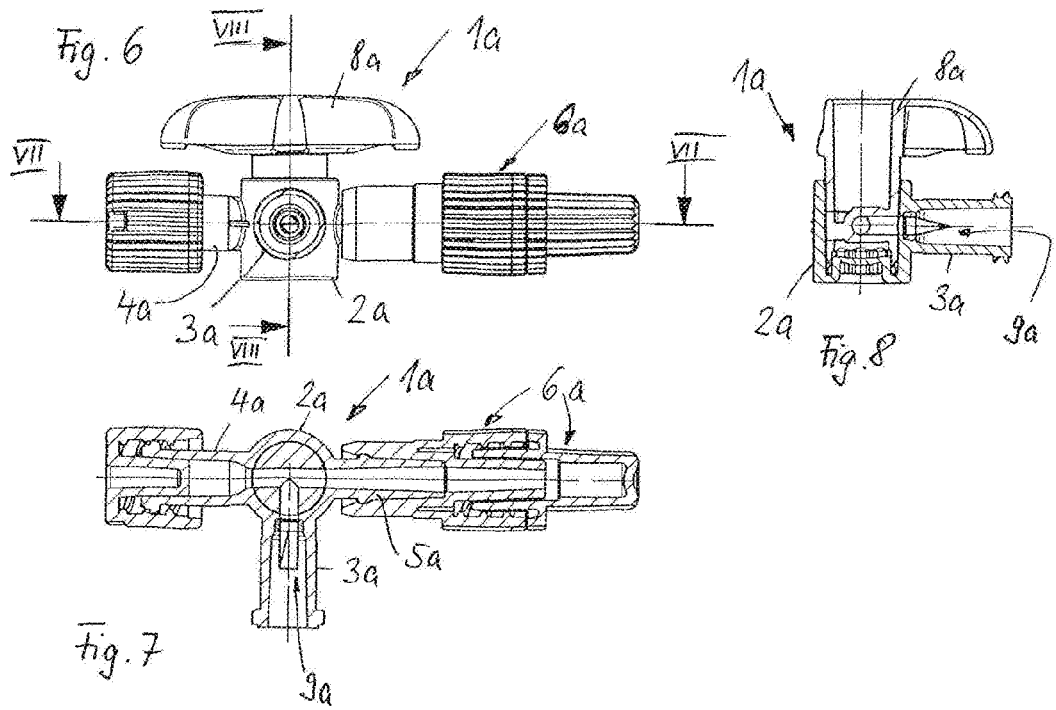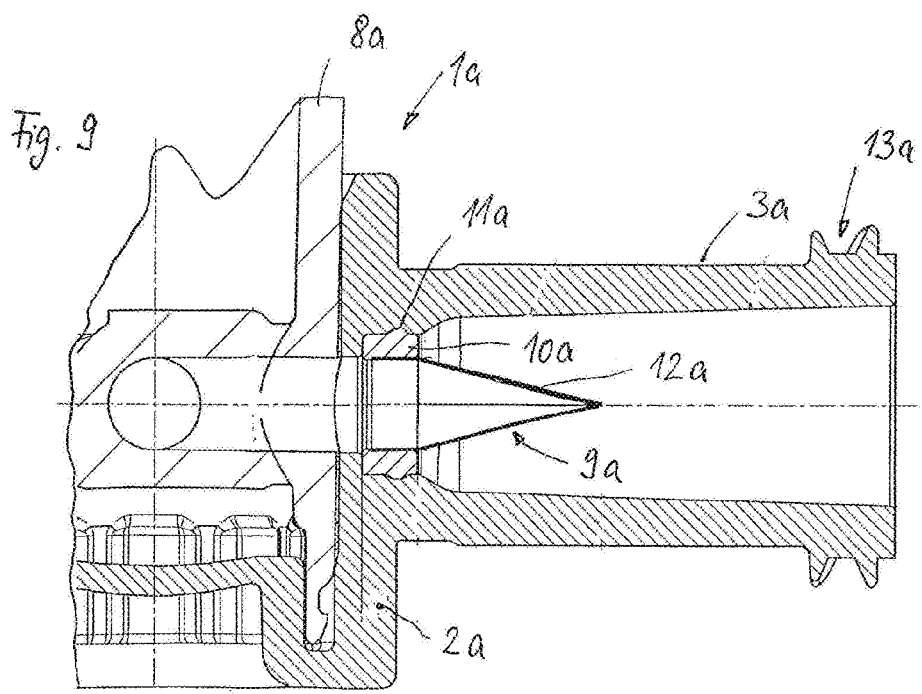

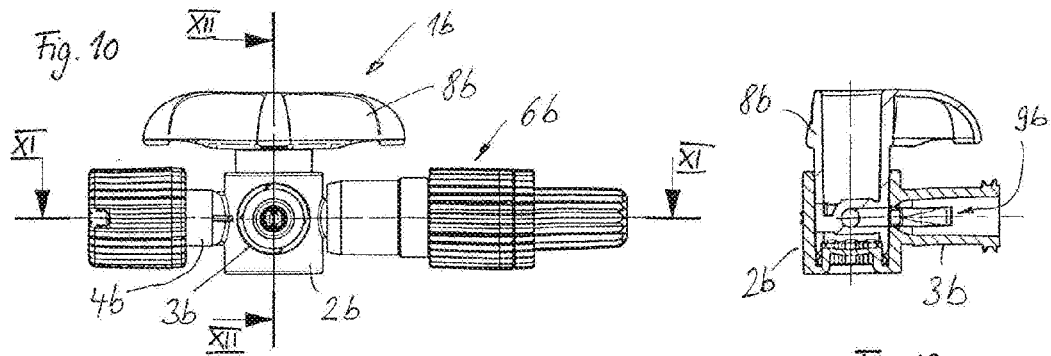
Fig. 10
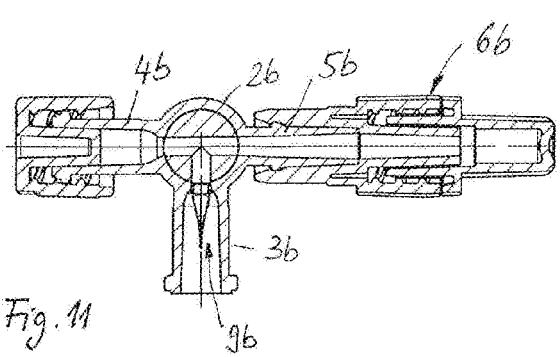
Fig. 12
Fig. 11
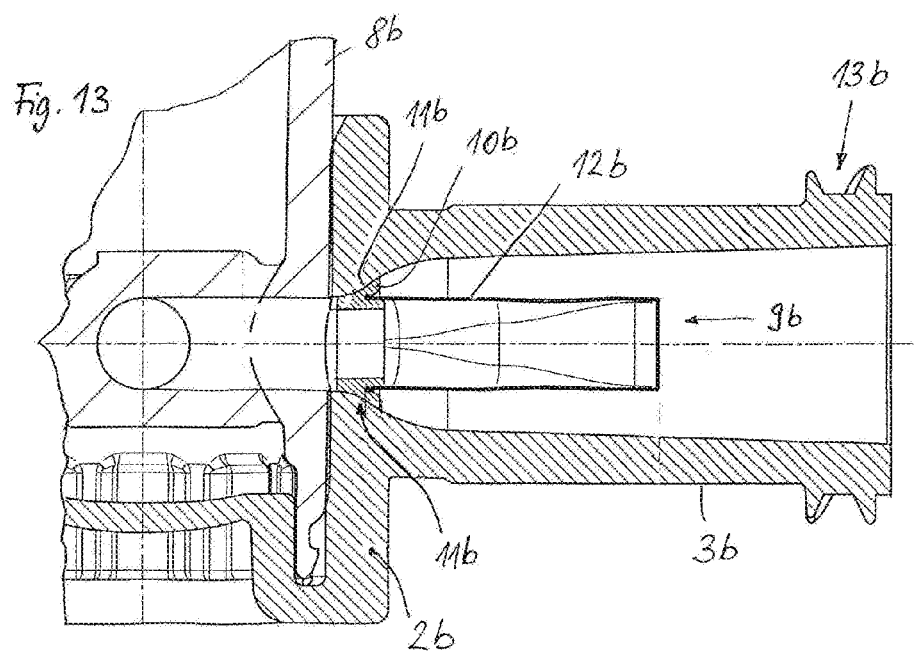
Fig. 13

MEDICAL FLUID CONTROL DEVICE AND A PARTICULATE FILTER FOR SAME

RELATED APPLICATIONS

This application is the United States national phase entry of International Application No. PCT/EP2016/053387, filed Feb. 17, 2016, which is related to and claims the benefit of priority of German Application No. 10 2015 203 863.7, filed Mar. 4, 2015. The contents of International Application No. PCT/EP2016/053387 and German Application No. 10 2015 203 863.7 are incorporated by reference herein in their entireties.

FIELD

The disclosure relates to a medical fluid control device for a medical fluid conduction system, with a fluid flow housing which has at least one attachment port for attaching and removing an external medical fluid-guiding component and at least one connection port for connecting to a further functional component of the medical fluid conduction system, and with an adjustment member for controlling a flow of fluid relative to the at least one attachment port and/or the at least one connection port, and to a particulate filter for same.

BACKGROUND

A medical fluid control device in the form of a three-way valve for a medical infusion system is generally known. A fluid control device of this kind is provided to be able to deliver medicaments to a patient line of a medical fluid conduction system. Corresponding drugs can be stored in fluid reservoirs that are made of glass or that have rubber closure stoppers. The medicaments to be administered can accordingly be contaminated with glass or rubber particles or other contaminants, caused during production or packaging or by the preparation for use, for example by piercing the stopper or breaking open the glass vials. The contamination of such administered medicaments with glass particles or rubber particles is known. To avoid such contaminants reaching the patient, provision is made that, when introducing such medicaments into a corresponding fluid line, filter components are inserted in-line between the fluid reservoir, which holds the medicaments, and the patient line. However, in routine clinical practice, it may happen that members of the medical personnel forget to insert suitable filter components between fluid reservoir and patient line.

SUMMARY

A medical fluid control device ensures that undesired entry of foreign particles is avoided upon attachment of a medical fluid-guiding component, in particular a fluid reservoir.

As regards the fluid control device, a particulate filter with a pore width of between 2 μm and 15 μm is integrated in the at least one attachment port and/or the at least one connection port. The particulate filter preferably has a pore width of 5 μm or greater. By integration of the particulate filter into the attachment port and/or the connection port, foreign particles possibly introduced via an external medical fluid-guiding component are retained in the attachment port. Entry into the medical fluid conduction system is reliably avoided. Thus, according to the invention, contamination of a patient line within the fluid conduction system by corresponding foreign particles is likewise avoided. The solution according to the invention is particularly advantageously suitable for use in a medical infusion system which comprises a patient line and in which the fluid control device is designed as a multiport plug valve, preferably as a three-way valve. A fluid flow housing of the medical fluid control device according to the invention is preferably produced from a suitable plastic, in particular from polyamide or polycarbonate. For the administration of cytostatics, a fluid flow housing made of polyamide is preferred, since polyamide has a sufficient resistance to stress. In a medical infusion system of this kind, a syringe is preferably provided as fluid-guiding component.

In one embodiment of the invention, the particulate filter is held in the attachment port or the connection port by force-fit and/or form-fit engagement and/or by material bonding. Preferably, the particulate filter is secured in the attachment port or the connection port by being pressed in (force-fit engagement), by being glued in (material bonding) or by being welded in (preferably by ultrasonic welding) (material bonding), or also by a preferably non-releasable latching connection (form-fit engagement).

In a further embodiment of the invention, the particulate filter is designed as a longitudinally extending hat body spatially inside the attachment port or the connection port. The design as a hat body ensures a large usable filter surface, such that blockage of the attachment port can be reliably avoided.

In a further embodiment of the invention, the hat body is designed as a hollow body open at one end, with a tapering configuration. In a tapering configuration of the hat body, the filter surface is designed either as constantly tapering or as tapering in sections, in particular as a filter surface tapering conically to a point. It is also possible to combine a hollow cylindrical filter surface with a filter surface tapering conically to a point. The corresponding filter surface is preferably supported by at least one carrier ring which is dimensionally stable in relation to the filter material of the filter surface and which, in addition to retaining the filter material, also serves to seal off the particulate filter inside the attachment port or the connection port.

In a further embodiment of the invention, the hat body has a tip narrowing to a point. Depending on the orientation of the hat body, captured foreign particles are thus concentrated in the area of the tip or externally in the area of an edge of the hat body opposite the tip.

In a further embodiment of the invention, the hat body has, at a front end area, a carrier ring which is secured on an inner wall of the attachment port or of the connection port. Like the fluid flow housing, the carrier ring is preferably produced from a suitable plastic, in particular from polyamide or polycarbonate, depending on the intended purpose. For the administration of cytostatics via the attachment port or the connection port, the carrier ring is advantageously produced from polyamide.

In a further embodiment of the invention, the particulate filter is secured in the attachment port or the connection port in such a way that the tip of the hat body is oriented distally or proximally with respect to an attachment area of the attachment port or of the connection port. The attachment port or the connection port is preferably provided with a Luer lock attachment. Depending on the particular design, the tip of the hat body can accordingly be directed into the interior of the fluid flow housing or outward in the direction of the outer attachment area of the attachment port or of the connection port.

In a further embodiment of the invention, the particulate filter comprises two carrier rings which are spaced apart axially from each other and between which extends a holding area for a filter surface. Advantageously, the holding area and the filter surface extend in an oblique plane running between the carrier rings. Particularly advantageously, the carrier rings spaced apart from each other have different external diameters. The different external diameters allow the particulate filter to be positioned in a conically tapering or conically widening channel of a corresponding attachment port or connection port. The particulate filter provided with the two carrier rings and with the holding area provided between these has a high degree of stability. At least one of the two carrier rings can be supported, inside a corresponding attachment port or connection port, on an annular shoulder of a corresponding flow channel of the connection port or of the attachment port.

In a further embodiment of the invention, the inner wall of the attachment port or of the connection port is provided with an annular profile which complements an annular outer contour of the carrier ring. The annular profile and the annular outer contour are adapted to each other in such a way that the carrier ring sits flush in the attachment port or the connection port, in order to obtain a secure seal between the particulate filter and the inner wall of the attachment port or of the connection port.

In a further embodiment of the invention, the annular profile is designed as an annular shoulder or as an annular wall with a constantly changing diameter, in particular as a conically shaped annular wall. An annular wall with a constantly changing diameter is preferably formed by a conically tapering or a conically widening annular wall. An annular shoulder is provided as an annular step in the area of the inner wall of the attachment port or of the connection port.

As regards the particulate filter, the particulate filter has the features relating to the particulate filter of at least one of the embodiments described above.

BRIEF DESCRIPTION OF THE DRAWING FIGURES

Further advantages and features of the invention will become clear from the claims and from the following description of preferred exemplary embodiments of the invention shown in the drawings.

Figure 15:
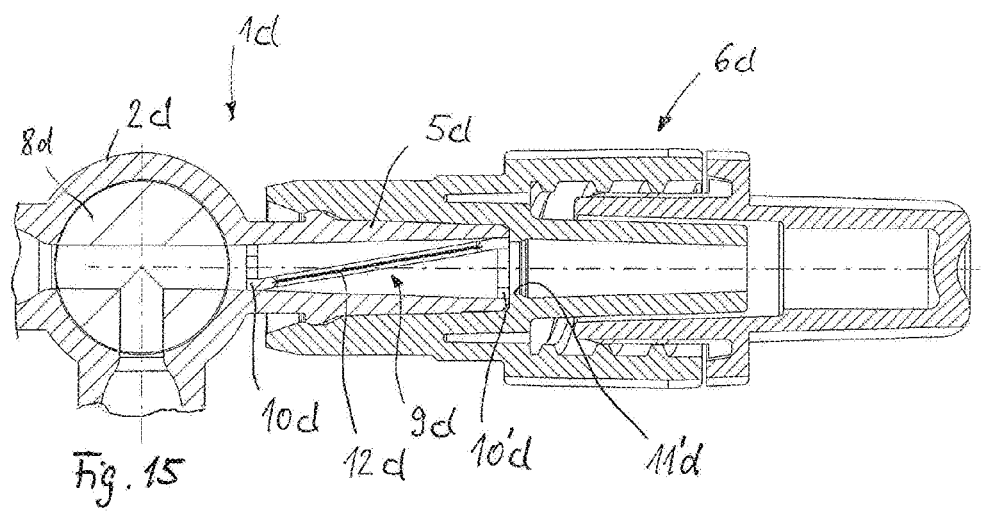
Figure 16:
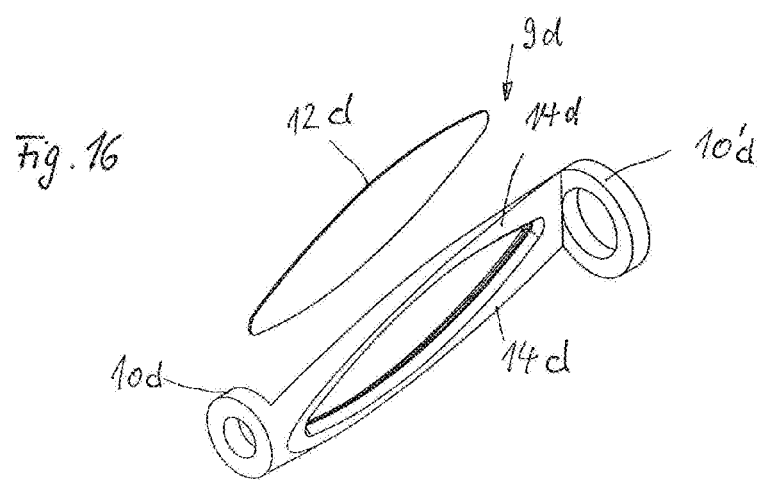

FIG. 1 shows a perspective exploded view of an embodiment of a medical fluid control device according to the invention, FIG. 2 shows a side view of the fluid control device according to FIG. 1, FIG. 3 shows a section through the fluid control device according to FIG. 2, along the section line III-III in FIG. 2, FIG. 4 shows a further sectional view of the fluid control device according to FIG. 2, along the section line IV-IV in FIG. 2, FIG. 5 shows an enlarged view of a detail of the view according to FIG. 4, FIG. 6 shows a side view of a further embodiment of a fluid control device according to the invention similar to FIG. 2, FIG. 7 shows a section through the fluid control device according to FIG. 6, along the section line VII-VII in FIG. 6, FIG. 8 shows a sectional view of the fluid control device according to FIG. 6, along the section line VIII-VIII in FIG. 6, FIG. 9 shows an enlarged detail of the sectional view according to FIG. 8, FIG. 10 shows a side view of a further embodiment of a fluid control device according to the invention, FIG. 11 shows a section through the fluid control device according to FIG. 10, along the section line XI-XI in FIG. 10, FIG. 12 shows a further sectional view of the fluid control device according to FIG. 10, along the section XII-XII in FIG. 10, FIG. 13 shows an enlarged detail of the sectional view according to FIG. 12, FIG. 14 shows a perspective exploded view of a further embodiment of a medical fluid control device according to the invention, FIG. 15 shows a sectional view of a partial area of the fluid control device according to FIG. 14 with an integrated particulate filter, and FIG. 16 shows a perspective exploded view of the particulate filter integrated in the fluid control device according to FIGS. 14 and 15.

DETAILED DESCRIPTION

A medical fluid control device, as shown on the basis of the various embodiments according to FIGS. 1 to 13, is designed as a three-way valve for a medical infusion system for administering drugs, in particular for administering cytostatics. The three-way valve 1, 1a, 1b according to FIGS. 1 to 13 is in each case provided with a fluid flow housing 2, 2a, 2b on which three ports 3, 4, 5; 3a, 4a, 5a; 3b, 4b, 5b are arranged protruding in different directions. An adjustment member 8, 8a, 8b is mounted in the fluid flow housing 2, 2a, 2b in such a way as to be movable in rotation about a vertical axis of the fluid flow housing 2, 2a, 2b. The adjustment member 8, 8a, 8b is also designated as plug. Fluid conduction channels (not shown in detail) are provided in the adjustment member 8, 8a, 8b and free or block a flow of fluid between the three ports 3, 4, 5; 3a, 4a, 5a; 3b, 4b, 5b depending on the position of the adjustment member 8. The port 3, 3a, 3b constitutes an attachment port within the meaning of the invention. The corresponding attachment port 3, 3a, 3b is described in more detail below with reference to the drawings. The two ports 4, 5; 4a, 5a; 4b, 5b constitute connection ports within the meaning of the invention. The connection port 4 is provided with a Luer lock attachment and serves to attach a further functional component of the fluid conduction system, in particular a fluid reservoir in the form of a bag with the medium (liquid) that is to be administered. The connection port 5 forms a connection to a patient line of the infusion system which leads to a patient who is undergoing treatment. The patient line is connected to the connection port 5 via corresponding attachment elements 6. An outer covering cap of the attachment elements 6 is removed here. An attachment element 6 secured on the connection port 5 is provided with a male Luer lock attachment, to which a complementary Luer lock attachment part of the patient line can be connected. The diametrically opposite connection port 4 is likewise provided with a closure cap 7, which is removed as soon as the connection port 4 is used.

A particulate filter 9, 9a, 9b is integrated in each attachment port 3, 3a, 3b of the various three-way valves 1, 1a, 1b according to FIGS. 1 to 13. The integration of the respective particulate filter 9, 9a, 9b is differently configured in the three embodiments. The differences are discussed below with reference to the drawings. In all of the embodiments, the respective particulate filter 9, 9a, 9b forms a hat body 12, 12a, 12b, which constitutes a three-dimensional shaped part oriented along a longitudinal extent of the attachment port 3. In all of the particulate filters 9, 9a, 9b, the hat body 12, 12a, 12b is designed tapering to a point. Each hat body 12, 12a, 12b is produced from a suitable filter material with a pore width of between 2 µm and 15 µm. Each hat body 12, 12a, 12b is held in a respective carrier ring 10, 10a, 10b. In the exemplary embodiments shown, the respective hat body 12, 12a, 12b is adhesively bonded into the respective carrier ring 10, 10a, 10b. The respective carrier ring 10, 10a, 10b, like the fluid flow housing 2, 2a, 2b, is made of polyamide.

A corresponding particulate filter can be integrated in the same way in the connection port 4, 4a, 4b.

In the embodiment according to FIGS. 1 to 5, the particulate filter 9 is held in the attachment port 3 with form-fit engagement. For this purpose, an annular shoulder is on the one hand provided in the area of an inner wall of the attachment port 3, on which annular shoulder the carrier ring 10 of the particulate filter 9 is axially supported. Moreover, the inner wall is provided in the area of the carrier ring 10 with a circumferential, trough-shaped annular groove, into which an annular profile of complementary shape in the area of an outer edge of the carrier ring 10 is latched. The annular shoulder and the annular groove in the area of the inner wall of the attachment port 3 constitute annular profiles within the meaning of the invention and serve to seal off the carrier ring 3 relative to the inner wall of the attachment port 3. An annular outer contour of the carrier ring 10 is accordingly adapted flush with the inner wall of the attachment port 3 in the area of the annular profile.

The annular shoulder of the inner wall of the attachment port 3 is positioned axially at a distance from the adjustment member 8, in such a way that a tip of the hat body 12 of the particulate filter 9, directed coaxially with respect to a central longitudinal axis of the attachment port 3 and inwardly toward the adjustment member 8, does not protrude into a path of rotational movement of the adjustment member 8. The tip of the hat body 12 ends directly in front of an outer contour of the adjustment member 8. The attachment port 3 is provided with an attachment area 13 at its distal front end area relative to the adjustment member 8, which attachment area 13 is designed as a female Luer lock attachment.

In the embodiment according to FIGS. 6 to 9, the three-way valve 1a has a particulate filter 9a which is integrated in the attachment port 3a and which comprises a hat body 12a directed out toward the attachment area 13a. In this embodiment, an annular profile 11a in the area of the inner wall of the attachment port 3a is offset proximally inward from the adjustment member 8a in relation to the embodiment according to FIG. 5. The annular profile 11a is designed in the same way as the annular groove in the inner wall, as is the case in the embodiment according to FIG. 5. Accordingly, it also serves in the same way for sealing purposes. The carrier ring 10a also has a complementary annular outer contour which ensures that the carrier ring 10a latches in the annular profile 11a of the inner wall of the attachment port 3a. From the carrier ring 10a, the hat body 12a protrudes in a longitudinal extent distally toward the attachment area 13a. Accordingly, the particulate filter 9a is oriented counter to the particulate filter 9 in the attachment port 3a.

It will be seen from FIGS. 3 and 7 that the tip of the respective hat body 12, 12a is not conical but instead designed tapering in a wedge shape, such that the tip defines an edge oriented transversely with respect to the longitudinal direction of the attachment port 3a.

In the embodiment according to FIGS. 10 to 13, the particulate filter 9b is integrated in the attachment port 3b by being materially bonded through welding or adhesion. For this purpose, an annular wall 11b of the inner wall of the attachment port 3b is designed with a constantly tapering cross section in the direction of the adjustment member 8b. The carrier ring 10b has a complementary annular outer contour, which ensures that the carrier ring 10b sits flush in the area of the annular wall 11b. The securing of the carrier ring 10b on the annular wall 11b is effected either by ultrasonic welding or by adhesive bonding using a suitable glue. The hat body 12b is inserted axially, with its front edge opposite its tip, into an axial annular groove of the carrier ring 10b and held therein likewise by material bonding through adhesion or welding. In the inserted state of the particulate filter 9b, both the annular wall 11b and also the carrier ring 10b are positioned on an end area of the attachment port 3b directed toward the adjustment member 8b, whereas the hat body 12b protrudes axially outward in the direction of the attachment area 13b. The attachment area 13b, which forms a distal front end area of the attachment port 3b relative to the adjustment member 8b, is also provided with a male Luer lock attachment.

The medical fluid control device according to FIGS. 14 to 16 is likewise designed as a three-way valve 1d and corresponds substantially to the embodiments described above. Sections and parts of the three-way valve 1d that are of identical construction or identical function are provided with the same reference signs but with the addition of the letter d. In order to avoid repetition in the description of the structurally identical and functionally identical parts and sections of the three-way valve 1d, reference is made to the disclosure of the above-described embodiments. The ways in which the three-way valve 1d differs from the above-described embodiments are discussed below.

An essential difference in the embodiment according to FIGS. 14 to 16 is that, in the three-way valve 1d, a particulate filter 9d is integrated in the connection port 5d. The connection port 5d has a flow channel that widens conically from the adjustment member 8d to an outer front end area. The attachment element 6d, which bears axially on the front end area of the connection port 5d by means of an annular shoulder 11'd, is latched onto the connection port 5d. The particulate filter 9d is integrated in the flow channel of the connection port 5d. The particulate filter 9d is formed by two mutually parallel carrier rings 10d and 10'd which are spaced axially apart from each other and which have different external diameters. Moreover, a circumferential contour of the carrier ring 10d is shaped conically in order to complement the inner contour of the flow channel of the connection port 5d. The external diameter of the carrier ring 10d is smaller than the external diameter of the axially spaced apart carrier ring 10'd. The carrier ring 10d and the carrier ring 10'd are connected to each other in one piece via a holding area 14d, which surrounds an elongate receiving opening. In the elongate receiving opening shown here, a filter material 12d is held which has a complementary elongate outer contour according to FIG. 19. Both the holding area 14d and also the filter material 12d extend at least substantially along a common plane, which runs obliquely between the carrier ring 10d and the carrier ring 10'd. The filter material 12d is clamped tightly in the holding area 14d. Moreover, the holding area 14d tightly surrounds the filter material 12d. The two carrier rings 10d and 10'd are provided with internal diameters of different sizes through which corresponding fluid flows inside the flow channel of the connection port 5*d* during operation of the three-way valve 1*d*, with corresponding particles being held back by the filter material 12*d* of the particulate filter 9*d*. The carrier ring 10'*d* bears axially against the annular shoulder 11'*d* of the attachment element 6*d*. Accordingly, during its assembly, the particulate filter 9*d* is inserted in a simple manner axially, with the smaller carrier ring 10*d* first, into the front end of the connection port 5*d*, until an outer edge of the carrier ring 10*d* is clamped tightly and with force-fit engagement on the inner contour of the flow channel of the connection port 5*d*, directly adjacent to the adjustment member 8*d*. The dimensions of the carrier rings 10*d* and 10'*d* are adapted to each other in such a way that the larger carrier ring 10'*d*, in the clamped position of the carrier ring 10*d*, is at least largely flush with the end face of the connection port 5*d*. As soon as the attachment element 6*d* is axially latched on, the annular shoulder 11'*d* secures the carrier ring 10'*d* axially in the connection port 5*d*. If the carrier ring 10'*d* still protrudes slightly past the end face of the connection port 5*d* before the attachment element 6*d* is latched on, the annular shoulder 11'*d* additionally presses the carrier ring 10'*d* axially into the connection port 5*d* by a small amount, as a result of which an additional clamping stress is applied to the particulate filter 9*d*, which further improves the securing of the particulate filter 9*d* and the seal inside the flow channel of the connection port 5*d*.

The invention claimed is:

1. A medical fluid control device for a medical fluid conduction system, the medical fluid control device comprising:
   a fluid flow housing having at least one attachment port configured to attach and remove an external medical fluid-guiding component and at least one connection port configured to connect to a further functional component of the medical fluid conduction system;
   an adjustment member configured to control a flow of fluid relative to the at least one attachment port and/or the at least one connection port; and
   a particulate filter material with a pore width of between 2 μm and 15 μm held in a fixed position within the at least one attachment port and/or the at least one connection port, and sealed against the at least one attachment port and/or the at least one connection port such that fluid must pass through the particulate filter material to pass through the at least one attachment port and/or the at least one connection port,
   wherein the particulate filter material is held in the fixed position within the at least one attachment port and/or the at least one connection port by a carrier ring that has an annular outer contour,
   wherein the at least one attachment port and/or the at least one connection port comprises an inner wall that has an annular groove, and
   wherein the annular outer contour of the carrier ring latches to the annular groove of the inner wall to secure the carrier ring in the at least one attachment port and/or the at least one connection port.

2. The medical fluid control device according to claim 1, wherein the particulate filter material is held in the fixed position in the at least one attachment port and/or the at least one connection port with force-fit and/or form-fit engagement and/or by material bonding.

3. The medical fluid control device according to claim 1, wherein the particulate filter material is formed as a longitudinally extending hat body extending from a first end to a second end, and is spatially inside the at least one attachment port and/or the at least one connection port.

4. The medical fluid control device according to claim 3, wherein the hat body comprises a hollow body that is open at the first end and tapers to a smaller size towards the second end.

5. The medical fluid control device according to claim 4, wherein the hat body tapers to a point at the second end.

6. The medical fluid control device according to claim 4, wherein the particulate filter material is secured in the at least one attachment port and/or the at least one connection port with the second end oriented distally or proximally with respect to an attachment area of the at least one attachment port and/or the at least one connection port.

7. The medical fluid control device according to claim 3, wherein the carrier ring is at the first end of the hat body.

8. The medical fluid control device according to claim 3, wherein the first end of the hat body is cylindrical shaped and the second end of the hat body is a single point.

9. The medical fluid control device according to claim 3, wherein the hat body is wedge shaped, with the second end of the hat body forming an edge transverse to a longitudinal direction of the at least one attachment port and/or the at least one connection port.

10. The medical fluid control device according to claim 3, wherein the second end of the hat body forms a tip that is coaxially aligned with a central longitudinal axis of the at least one attachment port and/or the at least one connection port.

11. A particulate filter for a medical fluid control device according to claim 1 comprising the features of the particulate filter of claim 1.

12. The medical fluid control device according to claim 1, wherein the at least one attachment port and/or the at least one connection port are integrally formed with the housing in a one-piece homogeneous body of unitary construction.

13. A medical fluid control device for a medical fluid conduction system, the medical fluid control device comprising:
   a fluid flow housing having at least one attachment port configured to attach and remove an external medical fluid-guiding component and at least one connection port configured to connect to a further functional component of the medical fluid conduction system;
   an adjustment member configured to control a flow of fluid relative to the at least one attachment port and/or the at least one connection port; and
   a particulate filter material with a pore width of between 2 μm and 15 μm held in a fixed position within the at least one attachment port and/or the at least one connection port, and sealed against the at least one attachment port and/or the at least one connection port such that fluid must pass through the particulate filter material to pass through the at least one attachment port and/or the at least one connection port,
   wherein the particulate filter material is provided on a particulate filter comprising:
   a first carrier ring configured to seal against a first region of the at least one attachment port and/or the at least one connection port;
   a second carrier ring spaced apart axially from the first carrier ring and configured to seal against a second region of the at least one attachment port and/or the at least one connection port;
   a filter holder extending between the first carrier ring and the second carrier ring; and wherein the particular filter material is secured to the filter holder and positioned in the axial direction between the first carrier ring and the second carrier ring such that fluid must pass through the particulate filter material to flow from the first carrier ring to the second carrier ring.

14. The medical fluid control device according to claim 13, wherein the filter holder and the particulate filter material extend in an oblique plane between the carrier rings.

15. The medical fluid control device according to claim 13, wherein the first carrier ring has a different external diameter than the second carrier ring.

16. A medical fluid control device for a medical fluid conduction system, the medical fluid control device comprising:
- a fluid flow housing having at least one attachment port configured to attach and remove an external medical fluid-guiding component and at least one connection port configured to connect to a further functional component of the medical fluid conduction system;
- an adjustment member configured to control a flow of fluid relative to the at least one attachment port and/or the at least one connection port; and
- a particulate filter material with a pore width of between 2 μm and 15 μm held in a fixed position within the at least one attachment port and/or the at least one connection port, and sealed against the at least one attachment port and/or the at least one connection port such that fluid must pass through the particulate filter material to pass through the at least one attachment port and/or the at least one connection port,
- wherein the particulate filter material is formed as a longitudinally extending hat body extending from a first end to a second end, and is spatially inside the at least one attachment port and/or the at least one connection port,
- wherein the hat body comprises a hollow body that is open at the first end and tapers to a smaller size towards the second end, and
- wherein the hat body tapers to a point at the second end.

17. A medical fluid control device for a medical fluid conduction system, the medical fluid control device comprising:
- a fluid flow housing having at least one attachment port configured to attach and remove an external medical fluid-guiding component and at least one connection port configured to connect to a further functional component of the medical fluid conduction system;
- an adjustment member configured to control a flow of fluid relative to the at least one attachment port and/or the at least one connection port; and
- a particulate filter material with a pore width of between 2 μm and 15 μm held in a fixed position within the at least one attachment port and/or the at least one connection port, and sealed against the at least one attachment port and/or the at least one connection port such that fluid must pass through the particulate filter material to pass through the at least one attachment port and/or the at least one connection port,
- wherein the particulate filter material is formed as a longitudinally extending hat body extending from a first end to a second end, and is spatially inside the at least one attachment port and/or the at least one connection port, and
- wherein the hat body has, at the first end, a carrier ring which is secured on an inner wall of the at least one attachment port and/or the at least one connection port to hold the particulate filter material at the fixed position.

* * * * *